United States Patent [19]

Polanyi et al.

[11] Patent Number: 5,458,128
[45] Date of Patent: Oct. 17, 1995

[54] METHOD AND APPARATUS FOR NONINVASIVELY MEASURING CONCENTRATION OF A DYE IN ARTERIAL BLOOD

[76] Inventors: Michael Polanyi; Thomas Polanyi, both of 105 Vaughn Hill Rd., Bolton, Mass. 01740

[21] Appl. No.: 261,634

[22] Filed: Jun. 17, 1994

[51] Int. Cl.$^6$ ........................................ A61B 6/00
[52] U.S. Cl. ...................... 128/654; 128/633; 128/664; 128/665; 356/39
[58] Field of Search ........................ 128/654, 655, 128/664, 665, 633; 600/3; 356/39–41; 250/339, 341, 351

[56] References Cited

U.S. PATENT DOCUMENTS

| | | | |
|---|---|---|---|
| 3,769,966 | 11/1973 | Youdin et al. | 128/654 |
| 3,998,550 | 2/1976 | Konishi et al. | |
| 4,281,645 | 8/1981 | Jöbsis | 128/633 |
| 4,361,049 | 11/1982 | Volgyesi | 128/654 |
| 4,372,294 | 2/1983 | Straus et al. | 128/654 |
| 4,759,369 | 7/1988 | Taylor | 128/664 |
| 4,819,752 | 4/1989 | Zelin | 128/664 |
| 5,024,231 | 6/1991 | Feldschuh et al. | 128/654 |
| 5,148,022 | 9/1992 | Kawaguchi et al. | 250/339.05 |
| 5,178,142 | 1/1993 | Harjunmaa et al. | 356/39 |
| 5,284,137 | 2/1994 | Kessler et al. | 128/665 |
| 5,372,135 | 12/1994 | Mendelson et al. | 356/39 |
| 5,377,674 | 1/1995 | Kuestner | 128/665 |
| 5,379,764 | 1/1995 | Barnes et al. | 356/39 |

OTHER PUBLICATIONS

Measurement of Cardiac Output in man by Dye Dilution Curves . . . , M. McGregor, et al, Circulation Research, vol. IX, Sep. 1961, pp. 1083–1088.

Use of Dichromatic Earpiece Densitometry For Determination Of Cardiac Output, John H. Reed, et al, 1966, pp. 373–380.

Primary Examiner—William E. Kamm
Assistant Examiner—Brian L. Casler
Attorney, Agent, or Firm—Michael J. Striker

[57] ABSTRACT

The method of noninvasively measuring concentration of a dye in a circulatory system includes measuring an optical density of an arterial blood-dye mixture in an artery as a function of time at a wavelength $\Gamma_1$ and at another different wavelength $\Gamma_2$; calculating ratios of optical density at the wavelength $\Gamma_1$ to that at wavelength $\Gamma_2$ of arterial blood in the artery at a time before a predetermined initial time and of the arterial blood-dye mixture at at least one time t after the predetermined initial time; injecting a dye absorbing electromagnetic radiation at at least one of the wavelengths into the circulatory system at the predetermined initial time, t=0, to form the arterial blood-dye mixture; measuring a hemoglobin concentration in a blood sample from the living organism; and calculating a concentration C(d,t) of the dye in the arterial blood-dye mixture as a function of time, t, from the hemoglobin concentration, Hb; from extinction coefficients, $\epsilon_{d1}$ and $\epsilon_{d2}$, of the dye at the wavelengths $\Gamma_1$ and $\Gamma_2$; and from the ratio R(0) at the time before the predetermined initial time and the ratio R(t) at the at least one time, t according to the following formula:

$$C(d,t) = \left( \frac{Hb(\epsilon_{r2} \epsilon_{o1} - \epsilon_{o2} \epsilon_{r1})(R(0) - R(t))}{\{R(0)(\epsilon_{r2} - \epsilon_{o2}) + \epsilon_{o1} - \epsilon_{r1}\}(R(t) \epsilon_{d2} - \epsilon_{d1})} \right)$$

wherein $\epsilon_{r1}$ and $\epsilon_{r2}$ are reduced hemoglobin extinction coefficients at wavelengths $\Gamma_1$ and $\Gamma_2$ respectively and $\epsilon_{o1}$ and $\epsilon_{o2}$ are oxyhemoglobin extinction coefficients at wavelengths $\Gamma_1$ and $\Gamma_2$ respectively.

18 Claims, 3 Drawing Sheets

METHOD AND APPARATUS FOR NONINVASIVELY MEASURING CONCENTRATION OF A DYE IN ARTERIAL BLOOD

BACKGROUND OF THE INVENTION

The present invention relates to a method and apparatus for measuring a concentration of a dye in arterial blood flowing in an artery in a living organism and, more particularly, to a method and apparatus for making measurements of dye concentration in arterial blood flowing in an artery in a noninvasive manner.

A method and apparatus for measuring dye concentration in arterial blood in living tissue can be used, for example, as part of a method of measuring cardiac output, i.e. the volume of blood pumped by the heart per unit time.

The measurement of cardiac output is an important clinical parameter which is routinely measured in clinical practice. A common procedure for measuring the cardiac output is based on the "indicator dilution" principle, namely: that the degree of dilution of the indicator injected in the circulating blood is a measure of the flow rate.

The method of measuring cardiac output which uses a dye as an indicator is the so-called "dye dilution" method. This method is briefly stated as follows: step a: arterial blood is withdrawn from the subject at constant speed via a catheter with a pump. The blood is made to flow through a recording spectrophotometric densitometer. This is an invasive time-consuming procedure performed by a trained physician assisted by a trained team of technicians, and it causes some pain and discomfort to the patient; and step b: a bolus of liquid containing a measured amount W of dye is rapidly injected into the blood circulation. The dye-arterial blood mixture flows through the densitometer and a recording of dye concentration as a function of time is obtained. The average concentration of the dye, C', in the arterial blood-dye mixture is then obtained from the relationship of dye concentration to time and the transit time $\Delta T$ of the mixture permits the cardiac output to be obtained by the well known formula of Hamilton et al:

$$CO = W/(C'x \Delta T) \quad (1)$$

To overcome the invasive and time consuming procedure of arterial blood withdrawal, step a), several investigators including M.McGregor et al in Circulation Research 9, pp. 1083–88(1961) and J. H. Reed, et al, J.Appl. Physiology 23, pp. 373–380(1967) used optical densitometers to measure and record the dye concentration in the arterial blood flowing in the pinna of the ear. The densitometers used for this purpose were modified ear oximeters used clinically to measure oxygen saturation.

This procedure was welcomed with enthusiasm in the field because of the noninvasive nature of the method of measuring concentration. However it was abandoned because of the many practical problems it presented including the need to vasodilate the earlobe and to calibrate the instrument.

A pulse oximetry apparatus for measuring the oxygen saturation of arterial blood is described in M. Konishi, T. Kisanuki, T. Yamanishi et al, U.S. Pat. No. 3,998,550 (1976). The oxygen saturation, O2Sat(0), is equal to the ratio, $C(0)/\{C(r)+C(0)\}$, that is the ratio of the concentration of oxyhemoglobin to the sum of the concentrations of the reduced form of hemoglobin and oxyhemoglobin, $Hb=C(r)+C(0)$. The novelty of this method and apparatus rests on the recognition that, when the optical density of a living body is measured with instruments having appropriately fast time response, the pulsatile phase of the optical density is representative of the optical density of arterial blood only. As known from the prior art, the ratio of the optical densities of arterial blood at two different wavelengths permits one to calculate the oxygen saturation of blood. By measuring this ratio of the optical densities of arterial blood, Konishi, et al, as cited above laid the foundation for the method of measuring oxygen saturation which is called "pulse oximetry". This noninvasive procedure is used widely today clinically in health care facilities for monitoring oxygen saturation.

The invention described hereinbelow is based on application of the methods of Konishi, et al, to the problem of measuring the concentration of a dye injected into arterial blood in living tissue as a function of time.

SUMMARY OF THE INVENTION

It is an object of the present invention to greatly simplify and expedite the invasive method of measuring the concentration of a dye indicator present in circulating arterial blood in a living organism as a function of time.

It is also an object of the present invention to provide an improved method of measuring dye concentration in a dye-arterial blood mixture flowing in an artery in a noninvasive manner which avoids the above-described disadvantages.

It is another object of the present invention to provide an improved apparatus for measuring dye concentration as a function of time in a dye-arterial blood mixture flowing in a living organism.

According to the present invention, the method of noninvasively measuring concentration of a dye in an arterial blood-dye mixture flowing in an artery of a circulatory system of a living organism after injection of the dye into the circulatory system includes measuring an optical density of arterial blood flowing in the artery of the living organism at a wavelength $\Gamma_1$ and at another wavelength $\Gamma_2$, both of these optical density values at these two different wavelengths being measured at a time before a predetermined initial time; injecting a dye absorbing electromagnetic radiation at at least one of the wavelengths into the circulatory system of the living organism at the predetermined initial time to form an arterial blood-dye mixture; measuring an optical density of the arterial blood-dye mixture flowing in the artery at the wavelength $\Gamma_1$ and at the wavelength $\Gamma_2$, these optical densities values being measured at at least one time after the predetermined initial time; calculating a ratio of the optical density value of the arterial blood measured at the wavelength $\Gamma_1$ to the optical density value of the arterial blood measured at the wavelength $\Gamma_2$ at the time before the predetermined initial time and a ratio of the optical density value of the arterial blood-dye mixture measured at the wavelength $\Gamma_1$ to the optical density value of the arterial blood-dye mixture measured at the wavelength $\Gamma_2$ at the at least one time after the predetermined initial time; measuring a hemoglobin concentration of the blood from the circulatory system of the living organism; and calculating a concentration of dye in the arterial blood-dye mixture at the at least one time after injecting the dye from the measured hemoglobin concentration of blood of the living organism, from extinction coefficients of the dye at the two different wavelengths and from the ratio of the two optical densities at the two different wavelengths measured before the predetermined initial time and the ratio of the optical densities at the two different wavelengths measured at the at least one time after the predetermined time. The method assumes that the oxygen saturation does not change during the time between measurements of the ratio of the optical densities.

This method advantageously includes storing in memory means a value of the ratio of optical densities at the time before the predetermined initial time to facilitate or permit the determination of the concentration of the dye at the at least one time after the predetermined initial time. In a preferred embodiment of the method the concentration of dye is calculated at any of a plurality of times after the predetermined initial time according to the following formula:

$$C(d,t) = \left[ \frac{Hb(\epsilon_{r2}\epsilon_{o1} - \epsilon_{o2}\epsilon_{r1})(R(0) - R(t))}{\{R(0)(\epsilon_{r2} - \epsilon_{o2}) + \epsilon_{o1} - \epsilon_{r1}\}(R(t)\epsilon_{d2} - \epsilon_{d1})} \right] \quad (2)$$

wherein $C(d,t)$=concentration of dye at the at least one time, t, after the predetermined initial time;

Hb=hemoglobin concentration, $R(t)$=ratio of optical densities at $\Gamma_1$ to $\Gamma_2$, at the at least one time, t, after the predetermined initial time, and $R(0)$=the ratio of optical densities at the time before the predetermined initial time;

$\epsilon_{ri}$=extinction coefficient of reduced hemoglobin at $\Gamma_i$ where i=1 or 2, $\epsilon_{oi}$=extinction coefficient of oxyhemoglobin at $\Gamma_i$ where i=1 or 2, and $\epsilon_{di}$=extinction coefficient of said dye at $\Gamma_i$ where i=1 or 2.

The above formula is derived by application of Beer's law for absorption of radiation passing through a body to the situation in which the pulsatile portion of the optical densities are measured in flowing arterial blood in which the dye is present.

The advantage of the method of the present invention is that it can be comparatively simply and easily performed using a device currently available for performing pulse oximetry to determine oxygen saturation level in the blood. There is no significant calibration problem with this noninvasive method.

The present invention also provides an apparatus for noninvasively measuring concentration of a dye present in arterial blood after injection in the circulatory system in a living organism comprising: means for measuring an optical density of an arterial blood flowing in an artery of the living organism at a wavelength $\Gamma_1$ and at another wavelength $\Gamma_2$ and at a time before a predetermined initial time at which a dye is injected into the arterial blood; means for measuring an optical density of an arterial blood-dye mixture flowing in the artery at the wavelength $\Gamma_1$ and at the wavelength $\Gamma_2$ and at at least one time after the predetermined initial time; means for calculating a ratio of the optical density of the arterial blood at the wavelength $\Gamma_1$ to the optical density of the arterial blood at the wavelength $\Gamma_2$ at the time before the predetermined initial time and a ratio of the optical density of the arterial blood-dye mixture at the wavelength $\Gamma_1$ to the optical density of the arterial blood-dye mixture at the wavelength $\Gamma_2$ at the at least one time after the predetermined initial time; and means for calculating a concentration of the dye in the arterial blood-dye mixture at the at least one time after the predetermined initial time from a predetermined hemoglobin concentration, Hb; from extinction coefficients of the dye at the wavelength $\Gamma_1$ and at the other wavelength $\Gamma_2$; and from the ratio at the time before the predetermined initial time and the ratio at the at least one time after the predetermined initial time.

The apparatus advantageously also includes memory means for storing the ratio of the optical densities at the one time before the predetermined initial time to facilitate the determining. The memory means is advantageously part of the processor means.

The apparatus advantageously includes a pulse ratio detector in one embodiment, a pulse oximeter in another embodiment and a modified pulse oximeter in another embodiment. These latter instruments are all commercially available and can be used together with conventional processor means equipped with analog to digital conversion devices and memory devices to assemble an apparatus for performing the method according to the invention. Thus, for example, instrumentation available for performing pulse oximetry to determine oxygen saturation can be also used to determine dye concentration of a dye in arterial blood after the dye is injected into the circulatory system. Knowledge of the relationship of dye concentration to time after injection in the flowing blood can be used in a variety of procedures, particularly those used to determine cardiac output or liver function. Thus considerable savings are obtained using the method of the invention, because existing commercially available, although comparatively expensive, equipment components can be assembled to provide the apparatus according to the invention.

The improved method of measuring cardiac output according to the invention is based on the method of measuring concentration of a dye injected into the circulatory system of the living organism as described above. The concentration of dye as a function of time is determined at a number of times after the initial predetermined time at which the dye is injected into the circulatory system. The average concentration of dye is used to determine the cardiac volume according to the formula:

$$co = W/(C' \times \Delta T) \quad (1')$$

wherein W is the amount of dye injected, C' is the average concentration of dye determined by averaging the concentration of dye as a function of time over the time and $\Delta T$ is the transit time of the arterial blood-dye mixture.

BRIEF DESCRIPTION OF THE DRAWING

The above described objects, features and advantages of the invention will now be described in detail in the following detailed description, with reference to the accompanying drawing in which.

DESCRIPTION OF THE PREFERRED EMBODIMENTS

Figure 1:
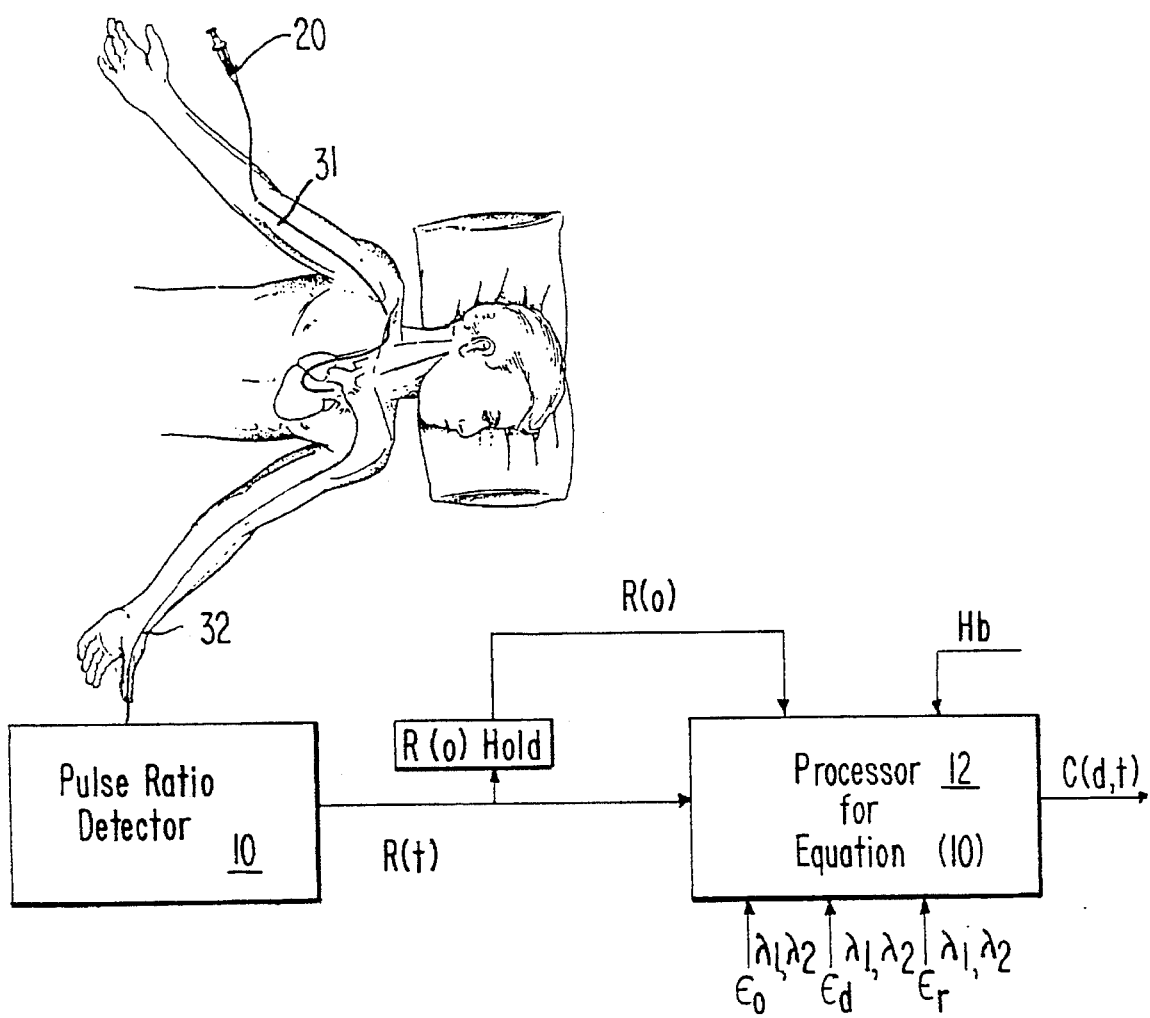
FIG. 1 is a schematic drawing showing a first embodiment of an apparatus for performing the method according to the invention using a pulse ratio detector to measure the time dependent ratio of optical densities at two different wavelengths.

The method of measuring the dye concentration of a dye present in arterial blood after being injected in the circulatory system of a living organism at at least one time after the time of injection of the dye is based on the measurement of the pulsatile phase of the optical densities measured at two different wavelengths. By the pulsatile phase of the optical density in the following is meant that portion of the optical density measured which oscillates with the frequency of the beating heart or pulse (See Konishi, loc. cit.). Throughout the following description the term "pulse ratio detector" denotes the techniques and instrumentation used to measure the ratio of the pulsatile phase of the optical density of living tissue containing the arterial blood in a living tissue at the two different wavelengths. The term "pulse oximeter" is used to denote an instrument based on these techniques whose output is the oxygen saturation of the blood as defined in the above background section.

In general, the optical densities of an arterial blood-dye mixture at two different wavelengths $\Gamma_1$ and $\Gamma_2$ are given by:

$$(O.D.)_1 = \epsilon_{o1} C(O)L + \epsilon_{r1} C(r)L + \epsilon_{d1} C(d,t)L \quad (3)$$

$$(O.D.)_2 = \epsilon_{o2} C(O)L + \epsilon_{r2} C(r)L + \epsilon_{d2} C(d,t)L \quad (4)$$

wherein $\epsilon_{ri}$=extinction coefficient of reduced hemoglobin at $\Gamma_i$ where i=1 or 2, $\epsilon_{oi}$=extinction coefficient of oxyhemoglobin at $\Gamma_i$ where i=1 or 2, and $\epsilon_{di}$=extinction coefficient of said dye at $\Gamma_i$ where i=1 or 2.

c(o)=oxyhemoglobin concentration;

c(r)=reduced hemoglobin concentration;

c(d,t)=dye concentration at time t and

L=optical path length.

The time dependent ratio, R(t), of the optical densities, $(O.D.)_1/(O.D.)_2$ is given by:

$$R(t) = \left[ \frac{\epsilon_{o1} C(O) + \epsilon_{r1} C(r) + \epsilon_{d1} C(d,t)}{\epsilon_{o2} C(O) + \epsilon_{r2} C(r) + \epsilon_{d2} C(d,t)} \right] \quad (5)$$

In the absence of dye in the arterial blood R(t)=R(0)

$$R(O) = \left[ \frac{\epsilon_{o1} C(O) + \epsilon_{r1} C(r)}{\epsilon_{o2} C(O) + \epsilon_{r2} C(r)} \right] \quad (6)$$

Measurements of the ratio R(t) and, separately, of the hemoglobin concentration, Hb, in the blood in the living tissue, which is equal to the sum of the concentrations of oxyhemoglobin and reduced hemoglobin $$Hb = C(O) + C(r), \quad (7)$$

permits one to solve the system of equations (3) and (4) for C(r) and C(0) in terms of the ratio R and Hb when C(d,t)=0. Equation (5) in conjunction with equation (6) leads to a result for C(d,t) in terms of R, C(0) and C(r):

$$C(O) = \left[ \frac{Hb(R(0)\epsilon_{r2} - \epsilon_{r1})}{R(0)(\epsilon_{r2} - \epsilon_{o2}) + \epsilon_{o1} - \epsilon_{r1}} \right] \quad (8)$$

$$C(r) = \left[ \frac{Hb(\epsilon_{o1} - R(0) \epsilon_{o2})}{R(0)(\epsilon_{r2} - \epsilon_{o2}) + \epsilon_{o1} - \epsilon_{r1}} \right] \quad (9)$$

$$C(d,t) = \left[ \frac{(\epsilon_{o2} C(O) - \epsilon_{r2} C(r))(R(0) - R(t))}{(R(t)\epsilon_{d2} - \epsilon_{d1})} \right] \quad (10a)$$

$$C(d,t) = \left[ \frac{(\epsilon_{o1} C(O) - \epsilon_{r1} C(r))(1 - R(t)/R(O))}{(R(t)\epsilon_{d2} - \epsilon_{d1})} \right] \quad (10a)$$

By introducing the values of C(0) and C(r) given by equations (8) and (9) into equations (10a) and (10b) the equation (10) hereinbelow is obtained which is a useful result for the dye concentration as a function of time from the time of injection of the dye in the circulatory system at t=0, the predetermined initial time. This result for the concentration as a function of time is given in terms of the measured ratio of optical densities R(t) and its value before the predetermined initial time, R(0), and the hemoglobin concentration which must be measured in a separate measurement as well as the extinction coefficients for the oxy-hemoglobin, the reduced hemoglobin and the dye at the two different wavelengths selected:

$$C(d,t) = \left( \frac{Hb\,(\epsilon_{r2}\epsilon_{o1} - \epsilon_{Po2}\epsilon_{r1})(R(0) - R(t))}{\{R(0)(\epsilon_{r2} - \epsilon_{o2}) + \epsilon_{o1} - \epsilon_{r1}\}(R(t)\epsilon_{d2} - \epsilon_{d1})} \right) \quad (10)$$

(i.e. equation (2) in the above summary).

The quantity R(0) which appears in formula (10) is assumed to remain constant during the time required to measure the dye concentration as a function of time.

An apparatus for measurement of dye concentration in the arterial blood as a function of time according to the method described above is shown in FIG. 1. The pulse ratio detector 10 is a known instrument (See Konishi, et al, cited above). Dye is injected into the circulatory system 31 of a patient at the predetermined initial time, t=0, with an injector means 20. The arterial-blood dye mixture formed flows in an artery 32 to an extremity, for example, the thumb as shown in FIG. 1, and the optical density ratios are measured with the pulse ratio detector 10. This instrument produces an output which is the ratio R(t). This output R(t) is fed directly to a processor 12 which calculates the value of C(d,t), e.g., from equation (10) and from the input extinction coefficients, the measured hemoglobin concentration which is available from standard clinical methods and the value of R(0) which is held in the memory circuit device, R(0) Hold, which is a commercially available sample and hold type circuit device 14. The processor 12 is a standard commercial processor with memory and analog-to-digital converter inputs for R(t) and R(0).

Another embodiment of the method and apparatus is based on a commercially available, but modified, pulse oximeter. The concentration of dye in the arterial blood-dye mixture can also be expressed as a function of the optical density ratios, R(0) and R(t), and the oxygen saturation O2sat(0) of the blood just before the predetermined initial time.

The fractional oxygen saturation of the arterial blood is given as follows:

$$O2sat(0) = C(O)/\{C(O) + C(r)\} \quad (11)$$

Introducing equation (7) and (11) into equation (10) the following result is obtain for the concentration of dye as a function of time in terms of the initial oxygen saturation in the blood, O2sat(0), $$C(d,t) = \left[ \frac{Hb\{O2Sat(0)\epsilon_{o1} + \{1 - O2Sat(0)\}\epsilon_{r1}\}\{1 - R(t)/R(0)\}}{R(t)\epsilon_{d2} - \epsilon_{d1}} \right] \quad (12)$$

Figure 2:
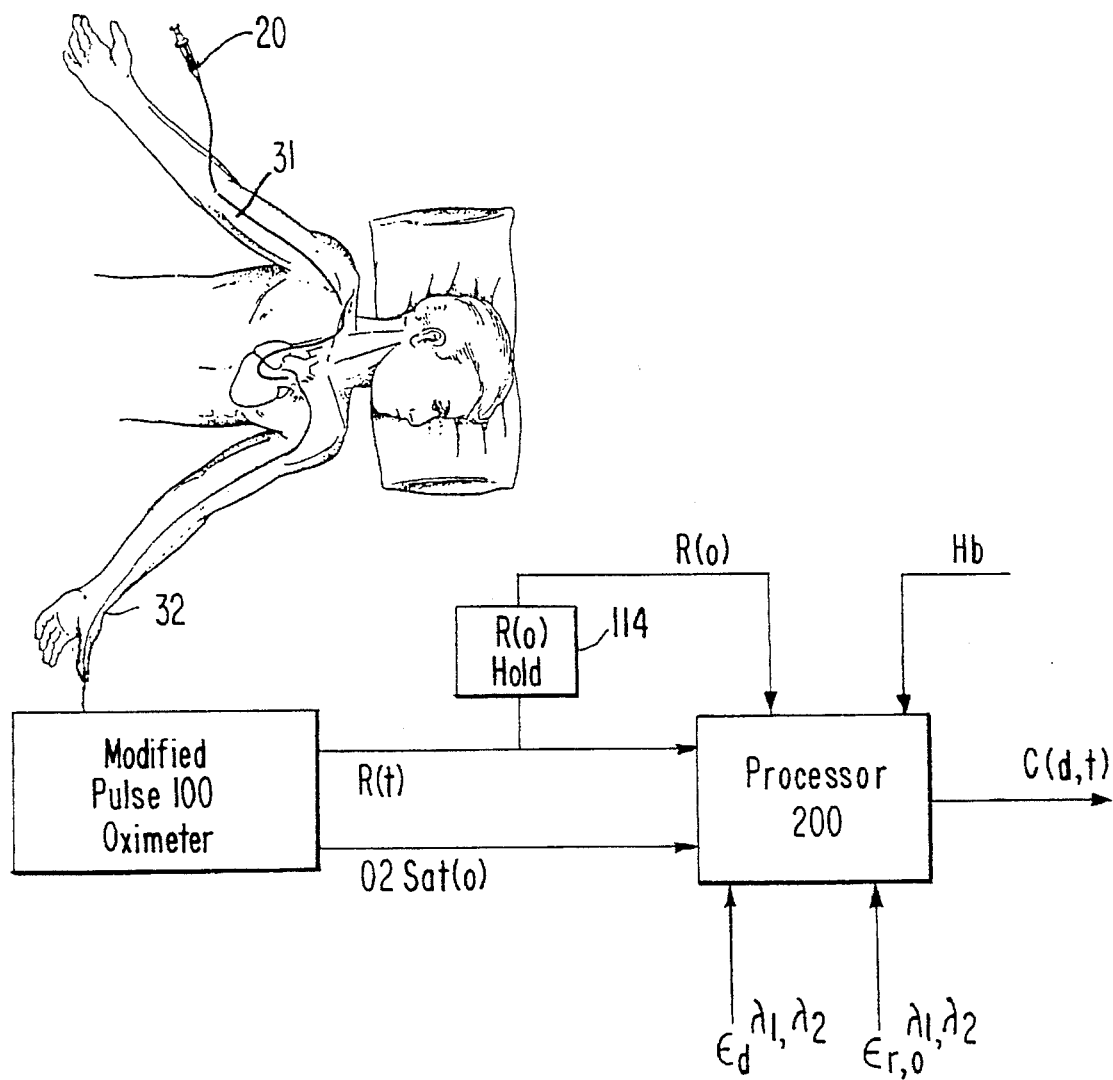
FIG. 2 is a schematic drawing of a second embodiment of an apparatus for performing the method according to the invention using a modified pulse oximeter to measure the time dependent ratio of optical densities at two different wavelengths and the oxygen saturation before the predetermined initial time.

The embodiment of the apparatus according to the invention utilizing equation (12) is illustrated in FIG. 2. The principal component of this apparatus is a pulse oximeter 100 which has been modified to output both R(t) and O2sat(0) which are fed to a standard processor 200 having A/D conversion. This apparatus is also provided with a sample and hold device 114, for retaining the value of R(0) for further processing. Conventional injecting means 120 is provided for injecting dye into the circulatory system 131 of a patient and the resulting arterial blood-dye mixture flows through an artery 132 to a location close to the modified pulse oximeter 100.

An additional embodiment of the invention is based on the concept of an apparent oxygen saturation value, O2sat(t), which is the value that a standard pulse oximeter would automatically output as the oxygen saturation at time t if the dye is injected at time t=0.

Introducing the values of C(O) and C(r) from equations (7) and (8) into equation (11) and solving for R(0) in terms of the oxygen saturation at time t=0, O2sat(0) one has $$R(0) = \Phi(O2Sat(0)) = \left[ \frac{O2Sat(0)(\epsilon_{o1} - \epsilon_{r1}) + \epsilon_{r1}}{O2Sat(0)(\epsilon_{o2} - \epsilon_{r2}) + \epsilon_{r2}} \right] \quad (13)$$

The ratio R(t) is the ratio of the optical densities of the arterial blood at time t after injection of the dye. This function can be obtained by introducing the values of the apparent oxygen saturation, O2sat(t), into equation (13), which value is directly measured in the standard pulse oximeter so that:

$$R(t) = \Phi'(O2Sat(t)) = \left[ \frac{O2Sat(t)(\epsilon_{o1} - \epsilon_{r1}) + \epsilon_{r1}}{O2Sat(t)(\epsilon_{o2} - \epsilon_{r2}) + \epsilon_{r2}} \right] \quad (14)$$

Introducing the functions $\Phi(O2Sat(0))$ and $\Phi'(O2Sat(t))$ in equation (12), equation (15) below is obtained which expresses the dye concentration as a function of the apparent oxygen saturation readings only, namely:

$$C(d,t) = \left[ \frac{Hb\{O2Sat(0)\epsilon_{o1} + \{1 - O2Sat(0)\}\epsilon_{r1}\}(1 - Z)}{\Phi'(O2Sat(t))\epsilon_{d2} - \epsilon_{d1}} \right] \quad (15)$$

wherein $Z = \Phi'(O2Sat(t))/\Phi(O2Sat(0))$

Figure 3:
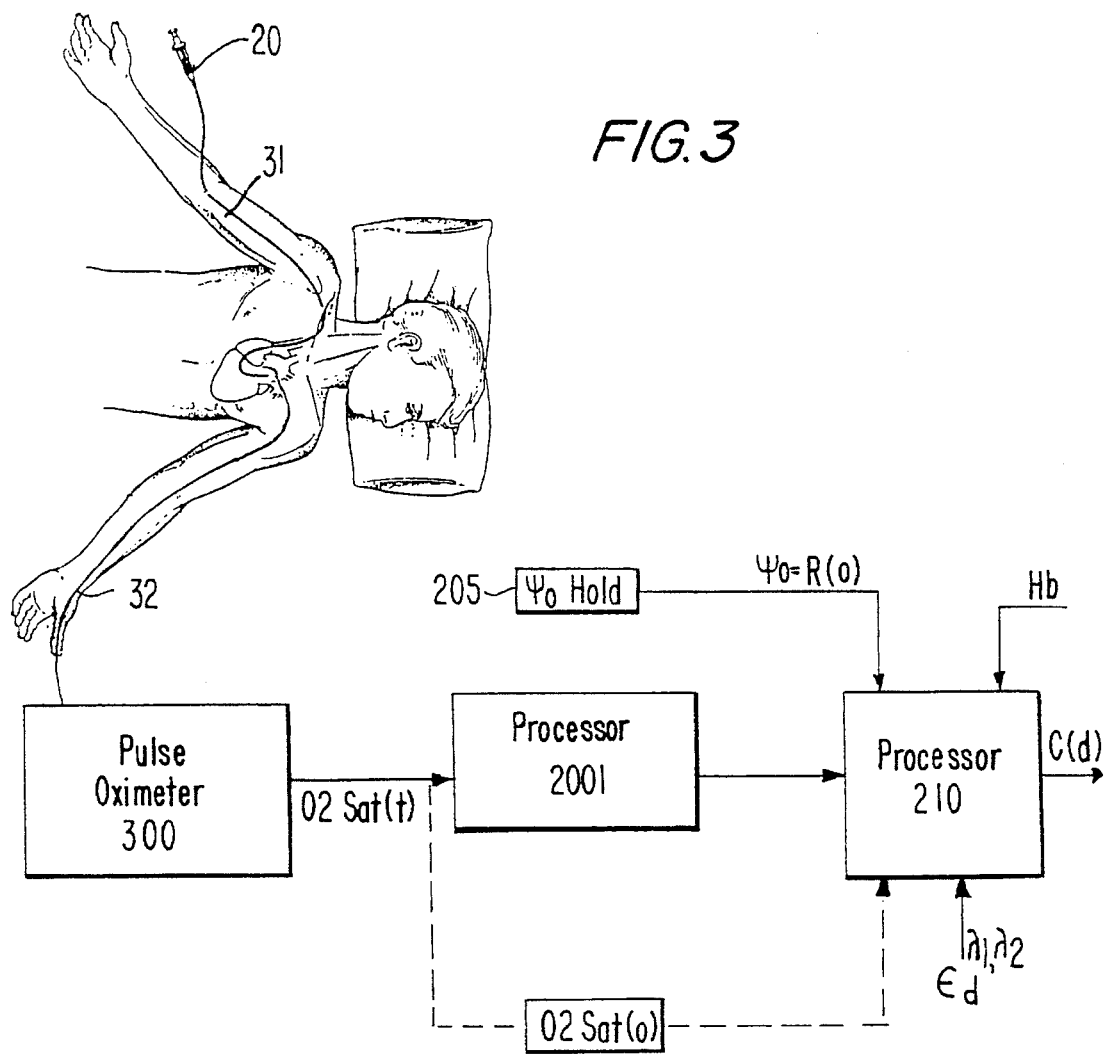
FIG. 3 is a schematic drawing of a third embodiment of an apparatus for performing the method according to the invention using a pulse oximeter to measure the apparent time dependent oxygen saturation.

FIG. 3 illustrates an embodiment of the apparatus based on the above equation (15) and the associated method. It includes a pulse oximeter 300 which produces O2sat(t), which is fed to a processor 200' and also to a sample and hold device or memory device 204 for the value of O2sat(0). The first processor 200' supplies a memory device 205 for $\Phi(O2Sat(0))$ which, in turn, supplies further processor means 210 for calculating equation (12) or (10), which requires the input of the extinction coefficients and the hemoglobin concentration. Conventional injecting means 220 is provided for injecting dye into the circulatory system 231 of a patient and the resulting arterial blood-dye mixture flows through an artery 232 to an extremity close to the pulse oximeter 300.

The method of the first embodiment shown in FIG. 1 is particularly simplified when $\epsilon_{o1} = \epsilon_{r1} = \epsilon_{o,r,805}$, i.e. when the isobestic point of hemoglobin, 805 nm, is selected as the $\Gamma_1$ wavelength in the method. Then equations (10), (12) and (15) are substantially simplified. In particular equation (10) becomes:

$$C(d,t) = \left[ \frac{Hb\,\epsilon_{o1}(R(0) - R(t))}{\epsilon_{d1}\,R(0)(R(t)\,\epsilon_{d2}/\epsilon_{d1} - 1)} \right] \quad (10c)$$

Further simplification is obtained when the extinction coefficient for the dye is selected to be 0 for the second wavelength. This second wavelength is advantageously 940 nm or some other wavelength at which the extinction coefficient of the dye is close to zero. Then assuming that $$\epsilon_{d2} \approx 0 \quad (16)$$

then equation (10) simplifies to $$C(d,t) = (\epsilon_{o1}/\epsilon_{d1})Hb\{(R(t) - R(0))/R(0)\} \quad (10d)$$

and equation (15) simplifies to equation (15'):

$$C(d,t) = (\epsilon_{o1}/\epsilon_{d1})Hb\{(O2Sat(t) - O2Sat(0))/(O2Sat(t) + \{\epsilon_{r2}/(\epsilon_{r2} - \epsilon_{o2})\})\} \quad (15)$$

Since Beer's law is not entirely valid for mixtures of unhemolized blood, it is not strictly applicable to situations where unhemolized blood is present. It is fully expected therefore that correction factors arrived at by experimental procedures will be needed to correct values for the dye concentration in flowing blood. The need for experimentally determined correction factors to complement the theoretical derivation such as the one above is well known to those skilled in the art.

While the invention has been illustrated and described as embodied in an apparatus and method for noninvasively measuring concentration of a dye present in arterial blood after injection in the circulatory system, it is not intended to be limited to the details shown, since various modifications and structural changes may be made without departing in any way from the spirit of the claimed invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. Method of noninvasively measuring concentration of a dye in a circulatory system of a living organism, said method comprising the steps of:

a) measuring an optical density of an arterial blood flowing in an artery of the living organism at a wavelength $\Gamma_1$ and at another wavelength $\Gamma_2$ and at a time before a predetermined initial time;

b) injecting a dye absorbing electromagnetic radiation at at least one of said wavelengths into the circulatory system of the living organism at said predetermined initial time to form an arterial blood-dye mixture;

c) measuring an optical density of said arterial blood-dye mixture flowing in said artery at said wavelength $\Gamma_1$ and at said wavelength $\Gamma_2$ and at at least one time after said predetermined initial time;

d) calculating a ratio of said optical density of said arterial blood at said wavelength $\Gamma_1$ to said optical density of said arterial blood at said wavelength $\Gamma_2$ at said time before said predetermined initial time and a ratio of said optical density of said arterial blood-dye mixture at said wavelength $\Gamma_1$ to said optical density of said arterial blood-dye mixture at said wavelength $\Gamma_2$ at said at least one time after said predetermined initial time;

e) measuring a hemoglobin concentration in a blood portion from said living organism; and f) calculating a concentration of said dye in said arterial blood-dye mixture at said at least one time after said predetermined initial time from said hemoglobin concentration determined by said measuring in step e), from extinction coefficients of said dye at said wavelength $\Gamma_1$ and at said other wavelength $\Gamma_2$ and from said ratios as calculated in step d) at said time before said predetermined initial time and at said at least one time after said predetermined initial time.

2. Method as defined in claim 1, further comprising storing in memory means a value of said ratio at said time before said predetermined initial time to facilitate said calculating of said concentration of said dye at said at least one time after said predetermined initial time.

3. Method as defined in claim 2, wherein said calculating of said concentration of said dye at said at least one time after said predetermined initial time is performed according to the following formula:

$$C(d,t) = \left[ \frac{Hb(\epsilon_{r2}\epsilon_{o1} - \epsilon_{o2}\epsilon_{r1})(R(0) - R(t))}{\{R(0)(\epsilon_{r2} - \epsilon_{o2}) + \epsilon_{o1} - \epsilon_{r1}\}(R(t)\epsilon_{d2} - \epsilon_{d1})} \right]$$

wherein $C(d,t)$=said concentration of said dye at said at least one time, t, after said predetermined initial time;

Hb=said hemoglobin concentration, $R(t)$=said ratio of the optical density at said wavelength $\Gamma_1$ to the optical density at said wavelength $\Gamma_2$ at the at least one time, t, after the predetermined initial time;

$R(0)$=said ratio of the optical density at said wavelength $\Gamma_1$ to the optical density at said wavelength $\Gamma_2$ at said time before the predetermined initial time;

$\epsilon_{ri}$=an extinction coefficient of reduced hemoglobin at said wavelength $\Gamma_i$ where i=1 or 2, $\epsilon_{oi}$=an extinction coefficient of oxyhemoglobin at said wavelength $\Gamma_i$ where i=1 or 2, and $\epsilon_{di}$=said extinction coefficient of said dye at said wavelength $\Gamma_i$ where i=1 or 2.

4. Method as defined in claim 3, further comprising selecting said wavelength $\Gamma_1$ so that said extinction coefficient, $\epsilon_{r1}$, for said reduced hemoglobin and said extinction coefficient, $\epsilon_{o1}$, for said oxyhemoglobin are equal and said extinction coefficient, $\epsilon_{d1}$, of said dye at said wavelength $\Gamma_1$ is much greater than said extinction coefficient, $\epsilon_{d2}$, of said dye at the other wavelength $\Gamma_2$ so that said concentration of said dye at said at least one time after said predetermined initial time is calculated according to the following formula:

$$C(d,t)=(\epsilon_{o1}/\epsilon_{d1})Hb\{(R(t)-R(0))/R(0)\}=(\epsilon_{o1}/\epsilon_{d1})Hb\{(O2Sat(t)-O2Sat(0))/(O2Sat(t)+\{\epsilon_{r2}/(\epsilon_{r2}-\epsilon_{o2})\})\}$$

wherein O2Sat(t) is an apparent oxygen saturation at the at least one time t after said predetermined initial time as measured by a pulse oximeter and O2Sat(0) is an oxygen saturation measured at said time before said predetermined initial time.

5. Method of noninvasively measuring concentration of a dye in a circulatory system of a living organism, said method comprising the steps of:

a) measuring an optical density of an arterial blood flowing in an artery of the living organism at a wavelength $\Gamma_1$ and at another wavelength $\Gamma_2$ and at a time before a predetermined initial time;

b) injecting a dye absorbing electromagnetic radiation at at least one of said wavelengths into the circulatory system of the living organism at said predetermined initial time to form an arterial blood-dye mixture;

c) measuring an optical density of said optical density of said arterial blood-dye mixture flowing in said artery at said wavelength $\Gamma_1$ and at said wavelength $\Gamma_2$ and at at least one time after said predetermined initial time;

d) calculating a ratio of said optical density of said arterial blood at said wavelength $\Gamma_1$ to said optical density of said arterial blood at said wavelength $\Gamma_2$ at said time before said predetermined initial time and a ratio of said optical density of said arterial blood-dye mixture at said wavelength $\Gamma_1$ to said optical density of said arterial blood-dye mixture at said wavelength $\Gamma_2$ at said at least one time after said predetermined initial time;

e) measuring a hemoglobin concentration, Hb, in a blood sample from said living organism;

f) calculating an oxyhemoglobin concentration, C(O), and a reduced hemoglobin concentration, C(r), in said arterial blood at said time before said initial predetermined time according to the following formulae:

$$C(O) = \left[ \frac{Hb(R(0)\epsilon_{r2} - \epsilon_{r1})}{R(0)(\epsilon_{r2} - \epsilon_{o2}) + \epsilon_{o1} - \epsilon_{r1}} \right]$$

$$C(r) = \left[ \frac{Hb(\epsilon_{o1} - R(0)\epsilon_{o2})}{R(0)(\epsilon_{r2} - \epsilon_{o2}) + \epsilon_{o1} - \epsilon_{r1}} \right]$$

wherein $\epsilon_{ri}$=an extinction coefficient of reduced hemoglobin at said wavelength $\Gamma_i$ where i=1 or 2, $\epsilon_{oi}$=an extinction coefficient of oxyhemoglobin at said wavelength $\Gamma_i$ where i=1 or 2, and g) calculating an oxygen saturation, O2Sat(0), in said arterial blood at said time before said predetermined initial time, wherein said oxygen saturation, O2Sat(0), is equal to C(O)/{C(O)+C(r)}; and h) calculating a concentration of said dye in said arterial blood-dye mixture at said at least one time after said predetermined initial time from said hemoglobin concentration, Hb; said oxygen saturation, O2Sat(0); extinction coefficients, $\epsilon_{d1}$ and $\epsilon_{d2}$, of said dye at said wavelengths, $\Gamma_1$ and $\Gamma_2$, and said ratio, R(0), at said time before said predetermined initial time and said ratio, R(t), at said at least one time after said predetermined initial time according to the following formula:

$$C(d,t) = \left[ \frac{Hb\{O2Sat(0)\epsilon_{o1} + \{1 - O2Sat(0)\}\epsilon_{r1}\}\{1 - R(t)/R(0)\}}{R(t)\epsilon_{d2} - \epsilon_{d1}} \right]$$

wherein $C(d,t)$=said concentration of said dye at the at least one time after the predetermined initial time.

6. Method as defined in claim 5, further comprising providing processor means for said calculating.

7. Method of noninvasively measuring concentration of a dye in a circulatory system of a living organism, said method comprising the steps of:

a) measuring an optical density of an arterial blood flowing in an artery of the living organism at a wavelength $\Gamma_1$ and at another wavelength $\Gamma_2$ and at a time before a predetermined initial time;

b) injecting a dye absorbing electromagnetic radiation at at least one of said wavelengths into the circulatory system of the living organism at said predetermined initial time to form an arterial blood-dye mixture;

c) measuring an optical density of said arterial blood-dye mixture flowing in said artery at said wavelength $\Gamma_1$ and at said wavelength $\Gamma_2$ and at at least one time after said predetermined initial time;

d) calculating a ratio of said optical density of said arterial blood at said wavelength $\Gamma_1$ to said optical density of said arterial blood at said wavelength $\Gamma_2$ at said time before said predetermined initial time and a ratio of said optical density of said arterial blood-dye mixture at said wavelength $\Gamma_1$ to said optical density of said arterial blood-dye mixture at said wavelength $\Gamma_2$ at said at least one time after said predetermined initial time;

e) measuring a hemoglobin concentration, Hb, in a blood sample from said living organism, said hemoglobin concentration being equal to a sum of an oxyhemoglobin concentration, C(O), and a reduced hemoglobin concentration, C(r);

f) calculating an oxygen saturation, O2Sat(0), in said arterial blood at said time before said predetermined initial time, wherein said oxygen saturation, O2Sat(0), is equal to C(0)/{C(0)+C(r)}, from the following formula:

$$R(0) = \left\{ \frac{O2Sat(0)(\epsilon_{o1} - \epsilon_{r1}) + \epsilon_{r1}}{O2Sat(0)(\epsilon_{o2} - \epsilon_{r2}) + \epsilon_{r2}} \right\}$$

wherein R(0) is said ratio of said optical density of said arterial blood at said wavelength $\Gamma_1$ to said optical density of said arterial blood at said wavelength $\Gamma_2$ at said time before said predetermined initial time;

g) calculating a concentration of said dye in said arterial blood-dye mixture in said living organism at said at least one time after said predetermined initial time from said hemoglobin concentration in said blood, Hb, as measured in step e); from said oxygen saturation, O2Sat(0), as calculated in step f); from extinction coefficients, $\epsilon_{d1}$ and $\epsilon_{d2}$, of said dye at said wavelengths, $\Gamma_1$ and $\Gamma_2$; and said ratio, R(0), of said optical density of said arterial blood at said wavelength $\Gamma_1$ to said optical density of said arterial blood at said wavelength $\Gamma_2$ at said time before said predetermined initial time and said ratio, R(t), of said arterial blood-dye mixture at said wavelength $\Gamma_1$ to said optical density of said arterial blood-dye mixture at said wavelength $\Gamma_2$ at said at least one time later than said predetermined initial time according to the following formula:

$$C(d,t) = \left[ \frac{Hb\{O2Sat(0)\epsilon_{o1} + \{1 - O2Sat(0)\}\epsilon_{r1}\}\{1 - R(t)/R(0)\}}{R(t)\epsilon_{d2} - \epsilon_{d1}} \right]$$

wherein

C(d,t)=said dye concentration at said at least one time t after said predetermined initial time.

8. Method as defined in claim 7, further comprising providing processor means for said calculating.

9. Method as defined in claim 8, further comprising providing memory means for storing a value, O2Sat(0), of said oxygen saturation at said time before said predetermined initial time and for storing a value of said ratio, R(0), of said optical densities of said arterial blood at said time before said predetermined initial time, said memory means being connected with said processor means.

10. Apparatus for noninvasively measuring concentration of a dye in a circulatory system of a living organism, said apparatus comprising:

means for measuring an optical density of an arterial blood flowing in an artery of the living organism at a wavelength $\Gamma_1$ and at another wavelength $\Gamma_2$ at a time before a predetermined initial time and for measuring an optical density of an arterial-blood dye mixture flowing in said artery at said wavelength $\Gamma_1$ and said other wavelength $\Gamma_2$ at at least one time after said predetermined initial time;

means for injecting said dye into the circulatory system of the living organism at said initial time to form said arterial blood-dye mixture, said dye having an extinction coefficient $\epsilon_1$ at said wavelength $\Gamma_1$ and an extinction coefficient $\epsilon_{d2}$ at said other wavelength $\Gamma_2$;

means for calculating a ratio of said optical density of said arterial blood at said wavelength $\Gamma_1$ to said optical density of said arterial blood at said other wavelength $\Gamma_2$ at said time before said predetermined initial time and a ratio of said optical density of said arterial blood-dye mixture at said wavelength $\Gamma_1$ to said optical density of said arterial blood-dye mixture at said other wavelength $\Gamma_2$ at said at least one time after said predetermined initial time; and means for calculating a concentration of said dye in said arterial blood-dye mixture at said at least one time after said predetermined initial time from a predetermined hemoglobin concentration, Hb; from said extinction coefficients of said dye at said wavelength $\Gamma_1$ and at said other wavelength $\Gamma_2$; and from said ratio at said time before said predetermined initial time and said ratio at said at least one time after said predetermined initial time.

11. Apparatus as defined in claim 10, wherein said means for measuring said optical densities at said wavelengths and said means for calculating said ratios are included in a pulse ratio detector.

12. Apparatus as defined in claim 11, wherein said means for calculating said concentration of said dye includes a processor and a memory connected to said processor, said memory includes means for storing said ratio at said time before said predetermined initial time and said processor and said memory are connected to said pulse ratio detector to receive said ratios from said pulse ratio detector.

13. Apparatus as defined in claim 10, further comprising means for selecting said wavelength $\Gamma_1$ so that an extinction coefficient, $\epsilon_{r1}$, for reduced hemoglobin and an extinction coefficient, $\epsilon_{o1}$, for oxyhemoglobin are equal and said extinction coefficient, $\epsilon_{d1}$, of said dye at said wavelength $\epsilon_1$ is much greater than said extinction coefficient, $\epsilon_{d2}$, of said dye at the other wavelength $\Gamma_2$ so that said concentration of said dye at said at least one time after said predetermined initial time is calculated according to the following formula:

$$C(d,t)=(\epsilon_{o1}/\epsilon_{d1})Hb\{(R(t)-R(0))/R(0)\} =(\epsilon_{o1}/\epsilon_{d1})Hb\{(O2Sat(t)-O2Sat(0))/(O2Sat(t)+\{\epsilon_{r2}/(\epsilon_{r2}-\epsilon_{o2})\})\}$$

wherein O2Sat(t) is an apparent oxygen saturation at the at least one time t after said predetermined initial time and O2Sat(0) is an oxygen saturation measured at said time before said predetermined initial time.

14. Apparatus as defined in claim 13, wherein said means for measuring said optical densities at said wavelengths, said means for calculating said oxygen saturation at said time before said predetermined initial time and said means for calculating said apparent oxygen saturation is included in a pulse oximeter.

15. Apparatus as defined in claim 14, wherein said means for calculating said concentration of said dye includes a processor and a memory connected to said processor, said memory includes means for storing said oxygen saturation at said time before said predetermined initial time and said processor and said memory are connected to said pulse ratio detector to receive said apparent oxygen saturation from said pulse oximeter.

16. Apparatus for noninvasively measuring concentration of a dye in a circulatory system of a living organism, said apparatus comprising:

means for measuring an optical density of an arterial blood flowing in an artery of the living organism at a wavelength $\Gamma_1$ and at another wavelength $\Gamma_2$ at a time before a predetermined initial time and for measuring an optical density of an arterial-blood dye mixture flowing in said artery at said wavelength $\Gamma_1$ and said other wavelength $\Gamma_2$ at at least one time after said predetermined initial time;

means for injecting said dye into the circulatory system of the living organism at said initial time to form said arterial blood-dye mixture, said dye having an extinction coefficient $\epsilon_1$ at said wavelength $\Gamma_1$ and an extinction coefficient $\epsilon_{d2}$ at said other wavelength $\Gamma_2$;

means for calculating a ratio of said optical density of said arterial blood at said wavelength $\Gamma_1$ to said optical density of said arterial blood at said other wavelength $\Gamma_2$ at said time before said predetermined initial time and a ratio of said optical density of said arterial blood-dye mixture at said wavelength $\Gamma_1$ to said optical density of said arterial blood-dye mixture at said other wavelength $\Gamma_2$ at said at least one time after said predetermined initial time;

means for calculating an oxyhemoglobin concentration, C(O), and a reduced hemoglobin concentration, C(r), in said arterial blood at said time before said initial predetermined time according to the following formulae:

$$C(O) = \left[ \frac{Hb(R(0)\epsilon_{r2} - \epsilon_{r1})}{R(0)(\epsilon_{r2} - \epsilon_{o2}) + \epsilon_{o1} - \epsilon_{r1}} \right]$$

-continued $$C(r) = \left[ \frac{Hb(\epsilon_{o1} - R(0)\epsilon_{o2})}{R(0)(\epsilon_{r2} - \epsilon_{o2}) + \epsilon_{o1} - \epsilon_{r1}} \right]$$

wherein $\epsilon_{ri}$=an extinction coefficient of reduced hemoglobin at said wavelength $\Gamma_i$ where i=1 or 2, $\epsilon_{oi}$=an extinction coefficient of oxyhemoglobin at said wavelength $\Gamma_i$ where i=1 or 2, and means for calculating an oxygen saturation, O2Sat(0), in said arterial blood at said one time before said predetermined initial time, wherein said oxygen saturation, O2Sat(0) is equal to C(O)/{C(O)+C(r)}; and means for calculating a concentration of said dye in said arterial blood-dye mixture at said at least one time after said predetermined initial time from a predetermined hemoglobin concentration, Hb; said oxygen saturation, O2Sat(0); extinction coefficients, $\epsilon_{d1}$ and $\epsilon_{d2}$, of said dye at said wavelengths, $\Gamma_1$ and $\Gamma_2$, and said ratio, R(O), at said time before said predetermined initial time and said ratio, R(t), at said at least one time after said predetermined initial time according to the following formula:

$$C(d,t) = \left[ \frac{Hb\{O2Sat(0)\epsilon_{o1} + \{1 - O2Sat(0)\}\epsilon_{r1}\}\{1 - R(t)/R(0)\}}{R(t)\epsilon_{d2} - \epsilon_{d1}} \right]$$

wherein

C(d,t)=said concentration of said dye at the at least one time t after said predetermined initial time.

17. Apparatus as defined in claim 16, wherein said means for measuring said optical densities at said wavelengths, said means for calculating said oxygen saturation at said time before said predetermined initial time and said means for calculating said ratios are included in a modified pulse oximeter.

18. Apparatus as defined in claim 17, wherein said means for calculating said concentration of said dye includes a processor and a memory connected to said processor, said memory includes means for storing said ratio at said time before said predetermined initial time, and said processor and said memory are connected to said pulse ratio detector to receive said ratios and said oxygen saturation at said time before said predetermined initial time from said modified pulse oximeter.

* * * * *